(12) United States Patent
Wagner et al.

(10) Patent No.: US 8,717,440 B2
(45) Date of Patent: May 6, 2014

(54) METHOD FOR EVALUATING MECHANICAL TESTS OF A COATING

(75) Inventors: Eva Wagner, Bad-Dürkheim (DE); Thomas Brinz, Bissingen A.D. Teck (DE); Thomas Geiger, Walddorfhaeslach (DE); Jane Lewis, Wales (GB); Markus Tiefenbacher, Fellbach-Schmiden (DE); Tobias Burk, Tuebingen (DE); Sebastian Koltzenburg, Dannstadt (DE); Wolfgang Schrof, Neuleiningen (DE)

(73) Assignees: Robert Bosch GmbH, Stuttgart (DE); BASF AG, Ludwigshafen (DE)

( * ) Notice: Subject to any disclaimer, the term of this patent is extended or adjusted under 35 U.S.C. 154(b) by 976 days.

(21) Appl. No.: 12/447,975

(22) PCT Filed: Sep. 11, 2007

(86) PCT No.: PCT/EP2007/059520
§ 371 (c)(1),
(2), (4) Date: Feb. 8, 2010

(87) PCT Pub. No.: WO2008/052835
PCT Pub. Date: May 8, 2008

(65) Prior Publication Data
US 2010/0149339 A1 Jun. 17, 2010

(30) Foreign Application Priority Data
Oct. 31, 2006 (DE) .......................... 10 2006 051 895

(51) Int. Cl.
*H04N 7/18* (2006.01)

(52) U.S. Cl.
USPC .............................. 348/164; 348/134; 427/8

(58) Field of Classification Search
USPC .................. 348/164, 134–135; 427/8–10
See application file for complete search history.

(56) References Cited

U.S. PATENT DOCUMENTS

| 8,182,719 | B2* | 5/2012 | Lubomirsky | 252/500 |
| 2005/0186328 | A1* | 8/2005 | Chatellier | 427/8 |
| 2007/0044397 | A1* | 3/2007 | Wiercinski et al. | 52/177 |
| 2011/0090332 | A1* | 4/2011 | Hing | 348/135 |

FOREIGN PATENT DOCUMENTS

EP 1 450 155 8/2004

OTHER PUBLICATIONS

Arruda, E.M., et al, "Effects of Strain Rate, Temperature and Thermomechanical Coupling on the Finite Strain Deformation of Glassy Polymers", Mechanics of Materials Netherlands, vol. 19, No. 2-3, Jan. 1995, pp. 193-212.

Honner, M., et al., "Thermography Analyses of the Hole-Drilling Residual Stress Measuring Technique", Infrared Physics and Technology Elsevier Netherlands, vol. 45, No. 2, Mar. 2004, pp. 131-142, XP00247619.

(Continued)

*Primary Examiner* — Bharat N Barot
(74) *Attorney, Agent, or Firm* — Kenyon & Kenyon LLP

(57) ABSTRACT

In a method for evaluating mechanical tests of a coating on a substrate, in a first step a mechanical stress is applied onto the coating, in a second step the substrate having the coating is isothermally clamped, in a third step an infrared photograph is generated of the region in which the mechanical stress is applied onto the coating in the first step, and in a fourth step the infrared photograph is evaluated. A device is arranged for carrying out the method.

12 Claims, 1 Drawing Sheet

(56) References Cited

OTHER PUBLICATIONS

Meola, C., et al. "Application if Infrared Thermography to Adhesion Science", Journal of Adhesion Science and Technology, Zeist, NL, vol. 20, No. 7, Jun. 2006, pp. 589-632.

International Search Report, PCT/EP2007/059520, dated May 8, 2008.

* cited by examiner

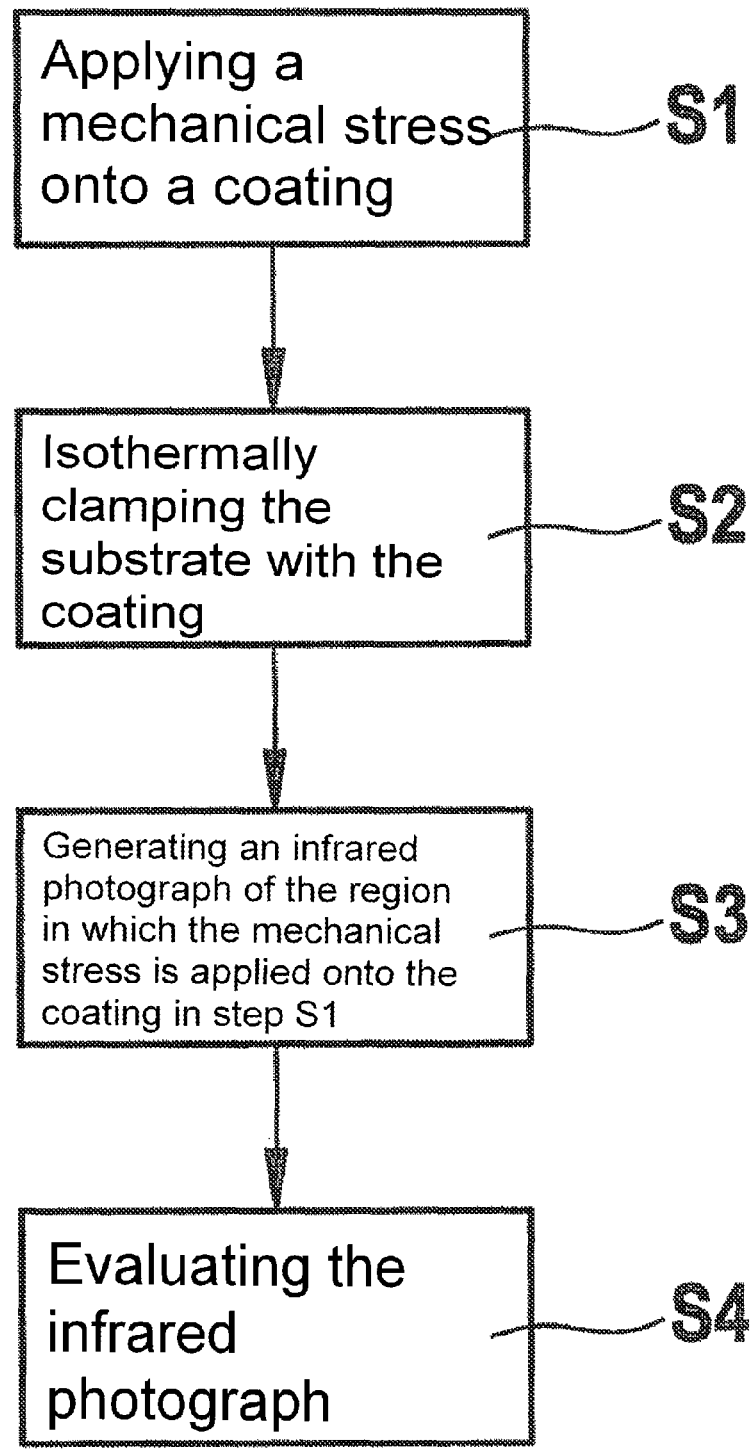

METHOD FOR EVALUATING MECHANICAL TESTS OF A COATING

FIELD OF THE INVENTION

The present invention relates to a method for evaluating mechanical tests of a coating on a substrate.

BACKGROUND INFORMATION

In order to determine the quality of coatings, various properties of the coatings are tested. Such coatings are for example lacquers on various surfaces, such as metals, plastics, glass, wood, etc. The tested mechanical properties include for example adhesion, elasticity, hardness, scratch resistance, or stone impact resistance of the lacquer. In general, the characterization of many testing methods takes place through the optical assessment of damages caused by a defined mechanical stress. Thus, for example the adhesion of a lacquer is usually tested using a cross cutting test. Here, as a rule the evaluation is carried out through visual observation and classification by the tester.

In the case of clear lacquers, the difference from the substrate is very small, so that even a visual evaluation by the tester is very difficult. U.S. Patent Application Publication No. 2004/0149026 describes mixing a fluorescent dye with the clear lacquer, so that fluorescent and non-fluorescent surfaces can be distinguished. However, a disadvantage of the admixture of a fluorescent dye is that the properties of the lacquer may be changed by the admixture.

In other conventional methods for determining the mechanical properties, the evaluation is carried out by the tester, and the methods are more empirical in nature. The evaluation is oriented towards clear differences in color. Evaluations of glossy or matte clear lacquers on glossy or matte metal substrates are limited by the slight color differences. A coloration of the clear lacquer due to the admixture of fluorescent dyes or other dyes in order to make the lacquer visible may change the hardening and/or the other properties of the lacquer due to interaction with the lacquer or with a component of the lacquer, e.g. the initiator. In addition, attention must be paid to solubility effects due to precipitation of the dye during the polymerization, and concomitant effects on the structure of the lacquer layer. In addition, a plurality of tests are frequently carried out for one coating, and the results may be altered by the admixture of the dye.

SUMMARY

The method according to example embodiments of the present invention for evaluating mechanical tests of a coating of a substrate includes the following steps:

(a) Applying a mechanical stress on the coating,
(b) Isothermal clamping of the substrate with the coating and generating an infrared photograph of the region in which the mechanical stress is applied onto the coating in step (a),
(c) Evaluation of the infrared photograph.

Through the infrared photograph, the infrared emission at a constant temperature is measured. Through the different degrees of emission of different materials, differing signals are recorded during the measurement of the infrared intensity. At the points at which the lacquer has become detached during the mechanical test, the emission intensity of the substrate is measured, and for coatings that adhere to the substrate the emission of the coating is measured. Thus, an advantage of the method is that due to the different emission properties it is no longer necessary to carry out an empirical estimation. In addition, it is also possible to test the properties of clear lacquers in an automated manner.

The mechanical stress is applied for example in the form of an elasticity test or an adhesion test of the coating. Here, the application of the stress takes place according to conventional methods as are currently used and empirically evaluated. The mechanical stress in step (a) can hear take place for example through cutting, shock, impact, tension, or pressure on the coating.

The mechanical stress applied in step (a) is for example a cross cutting, a penetration cupping, or an Erichsen cupping. In addition, the mechanical stress may also be applied by a falling ball, or by bending the substrate provided with the coating around a mandrel, the coating being situated on the side facing away from the mandrel.

For the cross cutting tests, first a plurality of parallel cuts are made in the coating. The cuts are made deep enough to reach down to the substrate. In general, six adjacent cuts are made.

Next, a series of parallel cuts are made in the coating that are oriented at 90° to the first cuts. Here as well, in general six adjacent cuts are made. The spacing between each two parallel cuts is here equally large, so that the cuts in the lacquer form 25 squares. After the cuts have been made, the treated surfaces are brushed off or pulled away using an adhesive strip. The quality of the adhesion of the coating results from the size of the portion of coating material that is broken off by the penetration of the cuts and removed by the brushing or the pulling off with the adhesive strip.

In the case of an Erichsen cupping test, first a test body, generally a hardened, polished steel ball having a diameter of 20 mm, is pressed into the rear side of the substrate with a uniform advance speed of approximately 0.2 mm/sec. Here, the rear side of the substrate is the side opposite the coating. The advance movement of the test body is terminated as soon as the first crack occurs in the surface of the coating.

In order to recognize the first occurrence of a crack in the coating, preferably the application of the mechanical stress onto the coating in step (a) and the generation of the infrared photograph in step (b) take place simultaneously. Here, the infrared photograph is preferably an infrared film that is generated continuously during the application of the mechanical stress. The simultaneous application of the mechanical stress onto the coating and the generation of the infrared photograph is preferably carried out during all mechanical tests in which a change in the coating must be recognized during the test.

In the case of mechanical tests in which an evaluation of the coating is not carried out until after the mechanical stress has terminated, it is sufficient for the mechanical stress to first be applied in step (a), and the infrared photograph to be generated subsequently in step (b). The methods in which the optical evaluation does not take place until after the application of the mechanical stress are for example the mechanical tests by which the adhesion of the coating on the substrate is tested.

In an embodiment, the evaluation of the infrared photograph is carried out by an electronic image processing system. The advantage of the evaluation using an electronic image processing system is that subjective impressions of the tester are not taken into account in the evaluation. An objective evaluation of the test is possible. A further advantage of the evaluation by an electronic image processing system is that the method according to example embodiments of the present invention is suitable for a series testing, in which a large number of coatings are tested in automated fashion.

BRIEF DESCRIPTION OF THE DRAWING

A method according to an example embodiment of the present invention is shown in schematically simplified form in the drawing in the form of a block diagram, and is explained in more detail in the following description.

DETAILED DESCRIPTION

The single FIGURE of the drawing shows a highly abbreviated flow diagram of the method according to an example embodiment of the present invention.

In a first step S1 shown in the FIGURE, a mechanical stress is applied onto a coating. Due to the mechanical stress, a substrate on which the coating is applied may become at least partly exposed due to detachment of the coating. However, it is also possible that, under defined conditions under which the stress is applied, no damage to the coating takes place. This is possible for example given high-quality lacquers.

A coating is for example a color-imparting lacquer or a clear lacquer that is applied onto the substrate. Furthermore, the coating may also be a plastic layer, a ceramic layer, or a powdered coating that is applied to the substrate. In addition, it is also possible for the coating to be a film glued onto the square. Furthermore, the coating may also be a vapor-deposited or electrochemically deposited layer, if the infrared emission differs from that of the substrate. Such a layer is for example a phosphating, as is carried out for example in order to provide rust protection on metallic surfaces, or is a metallic coating on a substrate made of plastic.

The substrate is preferably a plate. The material of the substrate is for example a metal, a plastic, glass, or ceramic. There is no limitation of the materials for the substrate. Care must merely be taken that the emission properties for infrared light of the coating and of the substrate are different.

In a second step S2, the substrate is isothermally clamped with the coating fashioned thereon. The isothermal clamping prevents different areas of the substrate with the coating fashioned thereon that have different temperatures from differently emitting the infrared radiation, thus causing errors in the image evaluation.

In the present context, isothermal clamping is understood to mean that the mount for the clamping, the substrate and the coating, and the surrounding air all have essentially the same temperature. Here, "essentially the same temperature" means that the temperature difference is not greater than 1 K.

Besides the sequence shown in FIG. 1, in which first the mechanical stress is applied to the coating and the substrate is subsequently clamped, it is also possible to exchange steps S1 and S2, that is, to first clamp the substrate with the coating, and then to apply the mechanical stress onto the coating.

In a third step S3, an infrared photograph is made of the region in which the mechanical stress is applied onto the coating in step S1. Due to the different degrees of emission of infrared radiation of different materials, from the infrared photograph the regions can be recognized in which there is no longer any coating material on the substrate.

Because the infrared radiation emission properties of a material differ as a function of temperature, it is necessary for the infrared photograph in step S3 to be made under isothermal conditions. Otherwise, given temperature differences in the coating or in the substrate it would be possible for warmer or colder regions to be interpreted as regions in which there was no longer any coating on the substrate, although the coating was in fact in order in this area. On the other hand, it would of course also be possible for the region having a different temperature in the infrared photograph to create the impression that the coating is in order at this location, although in fact there was no longer any coating on the substrate.

In order to achieve isothermal conditions for the infrared photograph, it is for example possible before generating the infrared photograph to wait until temperature differences that may exist in the substrate or in the coating have equalized themselves. It is preferable for the substrate to have only a small thickness, because in this case a homogenous temperature distribution arises more rapidly in the substrate.

In order to prevent temperature differences from being applied by the handling of the substrate with the coating when applying the mechanical stress, it is preferable to first clamp the substrate with the coating and then to exert the mechanical stress on the substrate. This prevents, for example, the substrate from being heated due to being held by the tester at the points at which the tester contacts the substrate.

The generation of the infrared photograph in step S3 can take place simultaneously with the application of the mechanical stress in step S1, or may take place only after the application of the stress in step S1. In the example embodiment shown here, the generation of the infrared photograph does not take place until after the stress has been applied. This is possible if the application of the stress causes changes in the coating, but it is not necessary to determine the time at which the changes occur. The generation of the infrared photograph in step S3 after the application of the mechanical stress is for example possible during the execution of a cross cutting in order to test the adhesion of the coating, a mandrel bending test in order to determine the bending elasticity, or a ball impact test in order to determine shock and impact elasticity.

In the mandrel bending test, the substrate with the coating fashioned thereon is bent around a conical mandrel. Subsequently, the diameter is determined at which the coating shows cracks or flakes off. In the ball impact test, a ball is dropped onto the coating. The ball is dropped onto the coating from different heights until cracks or detachment phenomena first become visible in the coating. It is thus possible first to drop the ball and then to generate an infrared photograph, and to repeat this process until a crack or a detachment of the coating is visible in the infrared photograph.

Of course, all other mechanical tests may be carried out in which the optical evaluation does not take place until after the stress.

In tests of the coating in which a continuously increasing stress is applied, in which the test is terminated as soon as cracks or detachment first appear in the coating, it is preferable that the infrared photograph be generated in step S3, while the application of the mechanical stress in step S1 takes place simultaneously. Such a test is for example an Erichsen cupping test in order to test the bending elasticity of the coating. In the Erichsen cupping test, for example, a ram is used to press a hardened polished steel ball, having a diameter of 20 mm, into the rear side of the substrate, fashioned as a test plate, with a constant advance speed of approximately 0.2 mm/sec until a first crack appears in the coating. The distance traveled by the plunger is read off as the cupping value. For this reason, it is important to recognize precisely the point in time at which the first crack appears in the coating. Therefore, it is necessary to generate infrared photographs at brief intervals of the area of the coating that is stressed by the Erichsen cupping test, while the test is being carried out. Particularly preferably, the infrared photographs are generated at intervals short enough that an infrared film is produced.

After the generation of the infrared picture, this photograph is evaluated in step S4. In the testing methods in which the infrared photograph is not generated until after the mechanical stress has been carried out, it is preferable first to generate the infrared photograph and subsequently to evaluate it. In the testing methods in which it is required to generate the infrared photograph simultaneously with the mechanical stress, the evaluation also preferably takes place essentially simultaneously with the generation of the photograph. The evaluation of the infrared photograph in step S4 can be made optically by a tester or in automated fashion by an image processing system. Preferably, the evaluation of the infrared photograph is carried out by an image processing system. The advantage of the image processing system is that the evaluation takes place objectively. Any subjective influence on the part of the tester is excluded. For the evaluation using an image processing system, any image processing system known to those skilled in the art may be used. It is required only that the image processing system recognize color differences. Thus, the image evaluation of the infrared photograph can take place either as a color image, the photograph preferably being separated into the individual color channels, or the grayscale images are evaluated.

For the evaluation, for example the surfaces in which the coating is visible are compared to the surfaces in which the substrate is visible, i.e. the coating has flaked off. As a result, the portion of the surface in which the coating has flaked off is indicated in %.

What is claimed is:

1. A method for evaluating mechanical tests of a coating on a substrate, comprising:
   (a) applying a mechanical stress onto the coating;
   (b) isothermally clamping the substrate with the coating and generating an infrared photograph of a region in which the mechanical stress is applied onto the coating in step (a); and
   (c) evaluation, by an electronic image processing system, of the infrared photograph.

2. The method according to claim 1, wherein the mechanical stress is applied in the form of at least one of (a) an elasticity test and (b) an adhesion test of the coating.

3. The method according to claim 1, wherein the mechanical stress in step (a) is applied onto the coating by at least one of (a) cutting, (b) shock, (c) impact, (d) tension, and (e) pressure.

4. The method according to claim 1, wherein the mechanical stress applied in step (a) at least one of (i) includes at least one of (a) a cross cutting, (b) a penetration cupping, and (c) an Erichsen cupping and (ii) is applied by at least one of (a) a falling ball and (b) bending the substrate provided with the coating around a mandrel, the coating being situated on a side of the substrate facing away from the mandrel.

5. The method according to claim 1, wherein the application of the mechanical stress onto the coating in step (a) and the generation of the infrared photograph in step (b) are performed simultaneously.

6. The method according to claim 5, wherein the infrared photograph is an infrared film that is generated continuously during the application of the mechanical stress.

7. The method according to claim 1, wherein first the mechanical stress is applied in step (a), and the infrared photograph is generated subsequently in step (b).

8. The method according to claim 1, wherein the evaluation of the infrared photograph is performed by an electronic image processing system.

9. The method according to claim 1, wherein the method is performed in automated fashion.

10. A device, comprising:
    a clamp device configured to clamp a substrate in order to apply a mechanical stress;
    an arrangement configured to apply the mechanical stress to the substrate clamped in the clamp device is applied to the substrate; and
    an infrared camera configured to generate an infrared photograph of the arrangement to apply the mechanical stress to the substrate clamped in the clamp device.

11. The device according to claim 10, wherein the clamp device, the arrangement, and the infrared camera are integrated in a single device.

12. The device according to claim 10, further comprising an evaluation unit configured to evaluate the infrared photographs.

* * * * *

UNITED STATES PATENT AND TRADEMARK OFFICE
CERTIFICATE OF CORRECTION

PATENT NO. : 8,717,440 B2  Page 1 of 1
APPLICATION NO. : 12/447975
DATED : May 6, 2014
INVENTOR(S) : Wagner et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1395 days.

Signed and Sealed this
Twenty-ninth Day of September, 2015

Michelle K. Lee
*Director of the United States Patent and Trademark Office*